(12) United States Patent
Bailey et al.

(10) Patent No.: US 6,171,308 B1
(45) Date of Patent: Jan. 9, 2001

(54) METHOD AND APPARATUS FOR EXTERNAL FIXATION OF LARGE BONES

(76) Inventors: Kirk Jay Bailey, 7 Crescent South, Andover, NJ (US) 07821; Sean P. Curry, 927 Castle Point Ter., Hoboken, NJ (US) 07030; John Scott Mahaffey, 57 Duck Hawk Ct., Hackettstown, NJ (US) 07840

(*) Notice: Under 35 U.S.C. 154(b), the term of this patent shall be extended for 0 days.

(21) Appl. No.: 08/918,218

(22) Filed: Aug. 25, 1997

Related U.S. Application Data

(62) Division of application No. 08/439,707, filed on May 12, 1995, now Pat. No. 5,662,650.

(51) Int. Cl.$^7$ .................................................. A61B 17/56
(52) U.S. Cl. .............................................................. 606/54
(58) Field of Search ............................... 606/54, 58, 59, 606/60, 61, 62

(56) References Cited

U.S. PATENT DOCUMENTS

| Re. 31,809 | 1/1985 | Danieletto et al. ................. 128/92 A |
| Re. 34,985 | 6/1995 | Pennig .................................... 606/58 |

(List continued on next page.)

FOREIGN PATENT DOCUMENTS

| 2213283 | 8/1973 | (DE) . |
| 203544 | 6/1939 | (FR) . |
| 448010 | 10/1974 | (SU) . |

OTHER PUBLICATIONS

EBI Medical Systems brochure, "New Ball Joint Articulating Ankle", 1 page, dated Jul., 1994.
EBI Medical Systems brochure, "If You Think Orthofix Is Just for Fractures . . . Think Again!", 1 page, dated Jan., 1994.
EBI Medical Systems brochure, "Orthofix Modulsystem Limb Reconstruction System", pp. 1–61, dated Apr., 1993.
EBI Medical Systems promotional material, "Orthofix Modulsystem Special Indications", pp. 1–56, undated.
EBI Medical Systems brochure, "The Pennig Dynamic Wrist Fixator" pp. 1–42, dated Jul., 1993.
EBI Medical Systems brochure, "Orthofix Modulsystem fixators", pp. 1–8 pages, undated.
EBI Medical Systems brochure, "Orthofix Modulsystem limb lengtheners", pp. 1–7 pages, undated.
EBI Medical Systems brochure, "Orthofix Modulsystem Small & mini fixators", pp. 1–7 pages, undated.
EBI Medical Systems brochure, "Challenging cases like these could drive you to distraction . . . callus distraction with the Limb Reconstruction System", 1–15 pages, dated Apr., 1993.
Biomet, Inc. brochure entitled "Hammer External Fixation System", 1 double–sided page, copyright 1994.
Biomet, Inc. brochure entitled "Hammer Mini–Tubular External Fixation Surgical Technique", 9 pgs., undated.

(List continued on next page.)

*Primary Examiner*—Michael Buiz
*Assistant Examiner*—(Jackie) Tan-Uyen T. Ho
(74) *Attorney, Agent, or Firm*—Harness, Dickey & Pierce, P.L.C.

(57) ABSTRACT

A fixator for securing a first bone portion in a position relative to a second bone portion. The fixator includes a first bone screw clamp that serves as a template for drilling a hole in a first bone portion and that secures the first bone screw to the fixator. The fixator also includes a second bone screw clamp that serves as a template for drilling a hole in the second bone portion and that secures the second bone screw to the fixator once the second bone screw is secured to the second bone portion. The fixator also includes a main body that is operable to secure the first bone screw clamp to the second bone screw clamp.

16 Claims, 7 Drawing Sheets

U.S. PATENT DOCUMENTS

| | | |
|---|---|---|
| 1,869,726 | 8/1932 | Youngren . |
| 1,997,466 | 4/1935 | Longfellow . |
| 2,020,262 | 11/1935 | Longfellow . |
| 2,055,024 | 9/1936 | Bittner, Jr. . |
| 2,238,870 | 4/1941 | Haynes . |
| 2,250,417 | 7/1941 | Ettinger . |
| 2,251,209 | 7/1941 | Stader . |
| 2,333,033 | 10/1943 | Mraz . |
| 2,346,346 | 4/1944 | Anderson . |
| 2,391,537 | 12/1945 | Anderson . |
| 3,547,113 | 12/1970 | Swanson ................................ 128/84 |
| 3,604,414 | 9/1971 | Borges et al. ...................... 128/92 D |
| 3,900,025 | 8/1975 | Barnes, Jr. ......................... 128/92 D |
| 3,961,854 | 6/1976 | Jaquet ..................................... 403/59 |
| 4,096,857 | 6/1978 | Cramer et al. ..................... 128/84 R |
| 4,127,119 | 11/1978 | Kronner ................................ 128/92 |
| 4,135,505 | 1/1979 | Day ....................................... 128/92 |
| 4,185,624 | 1/1980 | Gentile ............................... 128/92 A |
| 4,187,841 | 2/1980 | Knutson ................................. 128/92 |
| 4,244,360 | 1/1981 | Dohogne ................................ 128/92 |
| 4,258,708 | 3/1981 | Gentile .................................. 128/92 |
| 4,271,832 | 6/1981 | Evans et al. .......................... 128/92 |
| 4,299,212 | 11/1981 | Goudfrooy .......................... 606/96 X |
| 4,308,863 | 1/1982 | Fischer ............................... 128/92 A |
| 4,312,336 | 1/1982 | Danieletto et al. ................ 128/92 A |
| 4,360,012 | 11/1982 | McHarrie et al. ............... 128/92 EB |
| 4,450,834 | 5/1984 | Fischer ............................. 128/92 EB |
| 4,456,004 | 6/1984 | Kenny ................................ 128/92 A |
| 4,475,546 | 10/1984 | Patton ................................ 128/92 A |
| 4,483,334 | 11/1984 | Murray .............................. 128/92 A |
| 4,502,473 | 3/1985 | Harris et al. ...................... 128/92 A |
| 4,535,763 | 8/1985 | Jaquet ................................ 128/92 A |
| 4,541,422 | 9/1985 | de Zbikowski .................... 128/92 A |
| 4,548,199 | 10/1985 | Agee .................................. 128/92 A |
| 4,554,915 | 11/1985 | Brumfield .......................... 128/92 A |
| 4,564,007 | 1/1986 | Coombs et al. ................... 128/92 A |
| 4,570,625 | 2/1986 | Harris et al. ...................... 128/92 G |
| 4,573,459 | 3/1986 | Litton ................................ 128/92 A |
| 4,604,997 | 8/1986 | De Bastiani et al. ............. 128/92 A |
| 4,611,586 | 9/1986 | Agee et al. ........................ 128/92 A |
| 4,620,533 | 11/1986 | Mears ................................ 128/92 Z |
| 4,621,627 | 11/1986 | De Bastiani et al. ........... 128/92 ZZ |
| 4,628,919 | 12/1986 | Clyburn ........................... 128/92 ZK |
| 4,628,921 | 12/1986 | Rousso ............................... 128/92 Z |
| 4,628,922 | 12/1986 | Dewar ................................ 128/92 Z |
| 4,662,365 | 5/1987 | Gotzen et al. .................. 128/92 ZW |
| 4,696,293 | 9/1987 | Ciullo .............................. 128/92 ZK |
| 4,714,076 | 12/1987 | Comte et al. ................... 128/92 ZW |
| 4,730,608 | 3/1988 | Schlein ............................... 128/92 Z |
| 4,745,913 | 5/1988 | Castaman et al. ................ 128/92 W |
| 4,747,400 | 5/1988 | Koeneman et al. ............... 128/92 Z |
| 4,757,809 | 7/1988 | Koeneman et al. ............... 128/92 Z |
| 4,784,125 | 11/1988 | Monticelli et al. ................ 128/92 Z |
| 4,823,781 | 4/1989 | Buchanan .......................... 128/92 Z |
| 4,828,277 | 5/1989 | De Bastiani et al. ............. 279/15 G |
| 4,848,368 | 7/1989 | Kronner ............................. 128/92 Z |
| 4,869,242 | 9/1989 | Galluzzo ........................ 128/92 ZW |
| 4,895,141 | 1/1990 | Koeneman et al. ................. 606/54 |
| 4,922,896 | 5/1990 | Agee et al. ........................... 606/55 |
| 4,923,458 | 5/1990 | Fischer ................................. 606/59 |
| 4,941,481 | 7/1990 | Wagenknecht ....................... 606/59 |
| 4,942,872 | 7/1990 | Jawish ................................... 606/57 |
| 4,944,742 | 7/1990 | Clemow et al. ...................... 606/59 |
| 4,946,179 | 8/1990 | De Bastiani et al. ............. 279/1 SG |
| 4,978,348 | 12/1990 | LLizarov .............................. 606/57 |
| 4,988,349 | 1/1991 | Pennig ................................. 606/58 |
| 4,998,935 | 3/1991 | Pennig ................................. 606/54 |
| 5,019,077 | 5/1991 | De Bastiani et al. ................ 606/54 |
| 5,021,054 | 6/1991 | Monfardini et al. ................. 606/54 |
| 5,024,618 | 6/1991 | Tepic .................................... 606/53 |
| 5,026,372 | 6/1991 | Sturtzkopf et al. .................. 606/54 |
| 5,026,374 | 6/1991 | Dezza et al. ......................... 606/72 |
| 5,047,029 | 9/1991 | Aebi et al. ........................... 606/61 |
| 5,074,865 | 12/1991 | Fahmy ................................. 606/54 |
| 5,098,432 | 3/1992 | Wagenknecht ....................... 606/54 |
| 5,100,403 | 3/1992 | Hotchkiss et al. ................... 606/56 |
| 5,102,411 | 4/1992 | Kotchkiss et al. ................... 606/57 |
| 5,108,394 | 4/1992 | Kurokawa et al. .................. 606/59 |
| 5,112,331 | 5/1992 | Miletich .............................. 606/53 |
| 5,152,280 | 10/1992 | Danieli ................................ 128/54 |
| 5,160,335 | 11/1992 | Wagenknecht ....................... 606/59 |
| 5,167,661 | 12/1992 | Wagenknecht ....................... 606/54 |
| 5,192,281 | 3/1993 | de la Caffiniere ................... 606/59 |
| 5,203,783 | 4/1993 | Härle ................................... 606/53 |
| 5,207,676 | 5/1993 | Canadell et al. ..................... 606/54 |
| 5,209,750 | 5/1993 | Stef ..................................... 606/54 |
| 5,242,447 | 9/1993 | Borzone ............................... 606/73 |
| 5,275,599 | 1/1994 | Zbikowski et al. .................. 606/54 |
| 5,292,322 | 3/1994 | Faccioli et al. ...................... 606/59 |
| 5,300,072 | 4/1994 | Aghion ................................ 606/59 |
| 5,304,177 | 4/1994 | Pennig ................................. 606/58 |
| 5,314,426 | 5/1994 | Pohl et al. ............................ 606/58 |
| 5,320,622 | 6/1994 | Faccioli et al. ...................... 606/58 |
| 5,320,623 | 6/1994 | Pennig ................................. 606/59 |
| 5,330,474 | 7/1994 | Lin ...................................... 606/61 |
| 5,330,476 | 7/1994 | Hiot et al. ............................ 606/60 |
| 5,334,202 | 8/1994 | Carter .................................. 606/58 |
| 5,342,360 | 8/1994 | Faccioli et al. ...................... 606/59 |
| 5,380,322 | 1/1995 | van den Brink et al. ............ 606/57 |
| 5,620,442 | * 4/1997 | Bailey et al. ........................ 606/54 |
| 5,690,633 | * 11/1997 | Taylor et al. ........................ 606/73 |
| 5,743,898 | * 4/1998 | Bailey et al. ........................ 606/54 |
| 5,769,851 | * 6/1998 | Veith ................................... 606/57 |

OTHER PUBLICATIONS

Boanar, S.K., Marsh, J.L.; Unilateral External Fixation For Severe Pilon Fractures, Foot and Ankle, 14:57–64, 1993.

Marsh, J.L., Bonar S., Nepola, J.V., DeCoster, T.A., Hurwitz, S.R., Use of An Articulated External Fixator For Fractures of the Tibial Plafond; J Bone Joint Surg 77–A:1498–1509, 1995.

Fitzpatrick, D.C., Marsh, J.L., and Brown T.D.; Articulated External Fixation of Pilon Fractures: The Effects On Ankle Joint Kinematics; J. Orthop Trauma; 9:76–82, 1995.

Fitzpatrick, D.; Foels, W.S., Pedersen, D.R.; Marsh, J.L; Saltzman, C.L., Brown, T.D.; An Articulated Ankle External Fixation System That Can Be Aligned With the Ankle Axis; Iowa Orthop. Journal, vol. 15, 197–203, 1995.

Bottlang, M., Marsh, J.L., Brown, T.D.; Pathway of Instant Axes of Rotation of the Ankle Joint for the Application of External Articulated Fixation. Abstract, ASME 1997.

Bottlang, M., Marsh, J.L., Brown, T.D.; Articulated External Ankle Fixation: Effect of Hinge Axis Position on Joint Kinetics. ASB, 1997.

Synthes brochure, The AO/ASIF Hybrid Fixator (Technical Guide), 13 pgs., undated.

Paper entitled "Hybrid Application", pp. 15, 17, 19, 21,23, 25, undated.

Brochure entitled Monticelli Spinelli External Fixation System, 2 pgs., (undated).

Ace brochure entitled "Wire Tension Treatment of Complex Tibial Plateau & Pilon Fractures", pp. 1, 3, 5, 7 (undated).

Orthofix Modulsystem brochure entitled "The Orthofix Periarticular Module", 7 pgs., (undated).

* cited by examiner

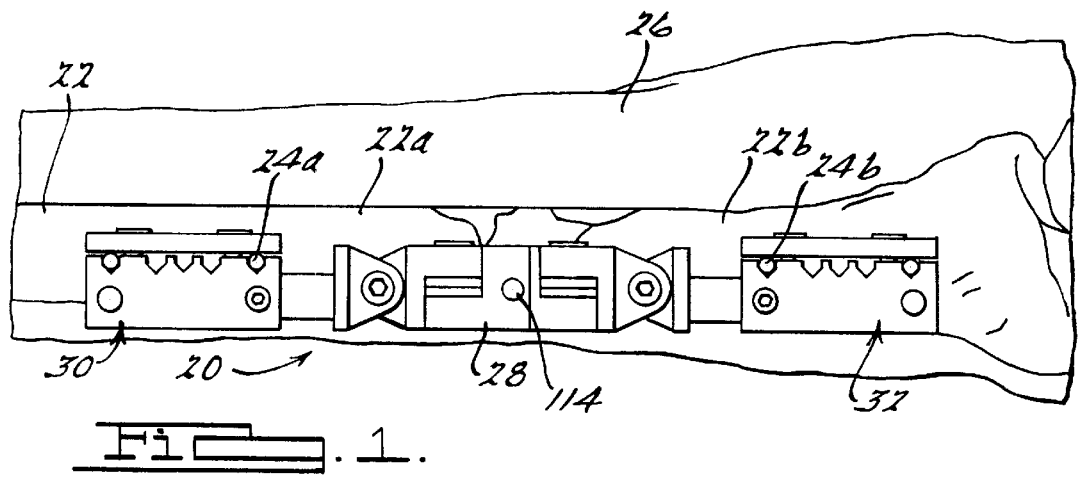
FIG. 1.
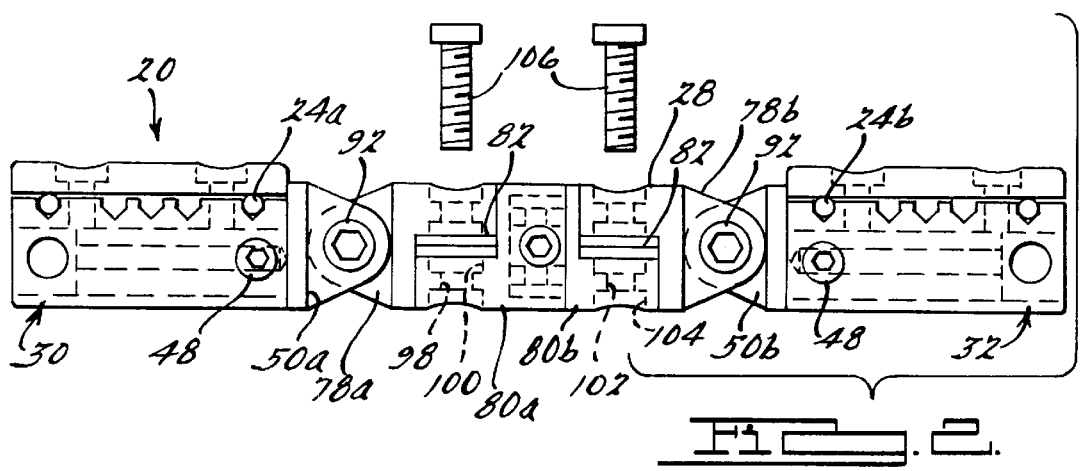
FIG. 2.
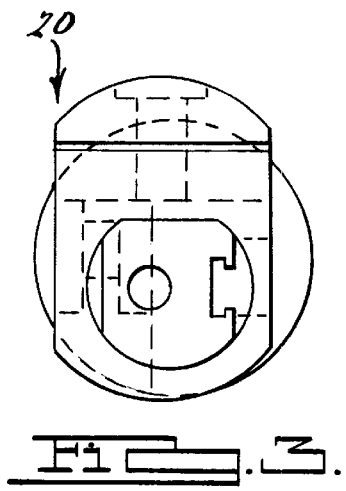
FIG. 3.
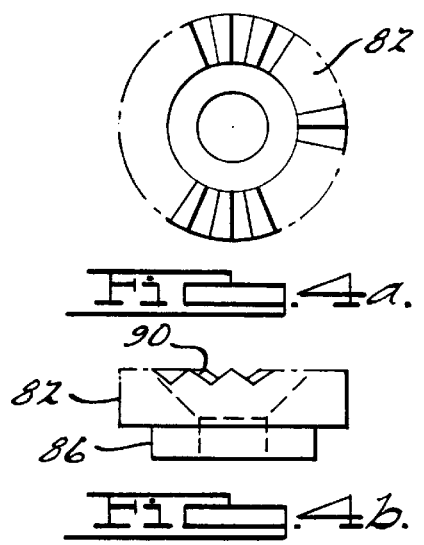
FIG. 4a.
FIG. 4b.

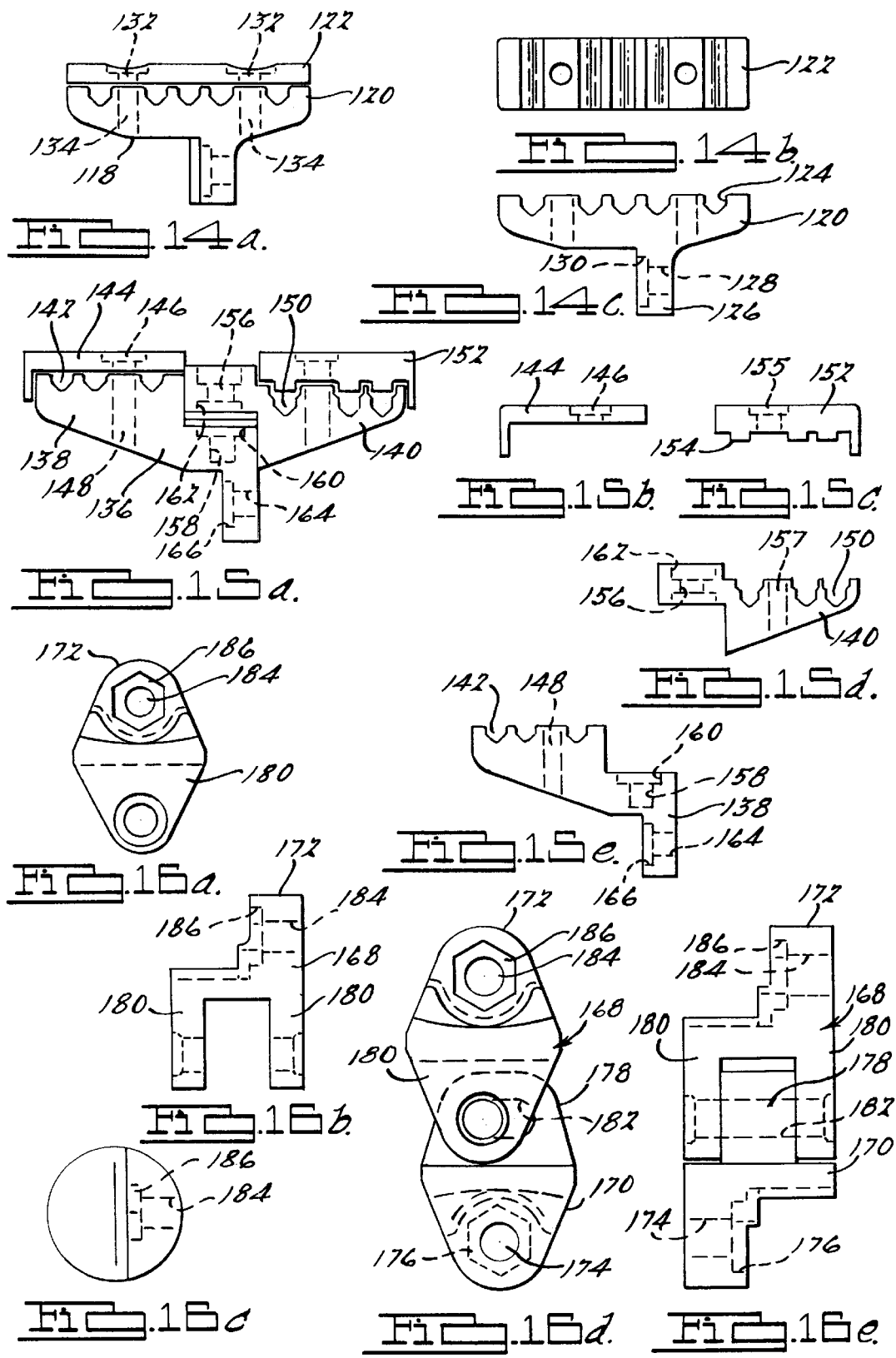

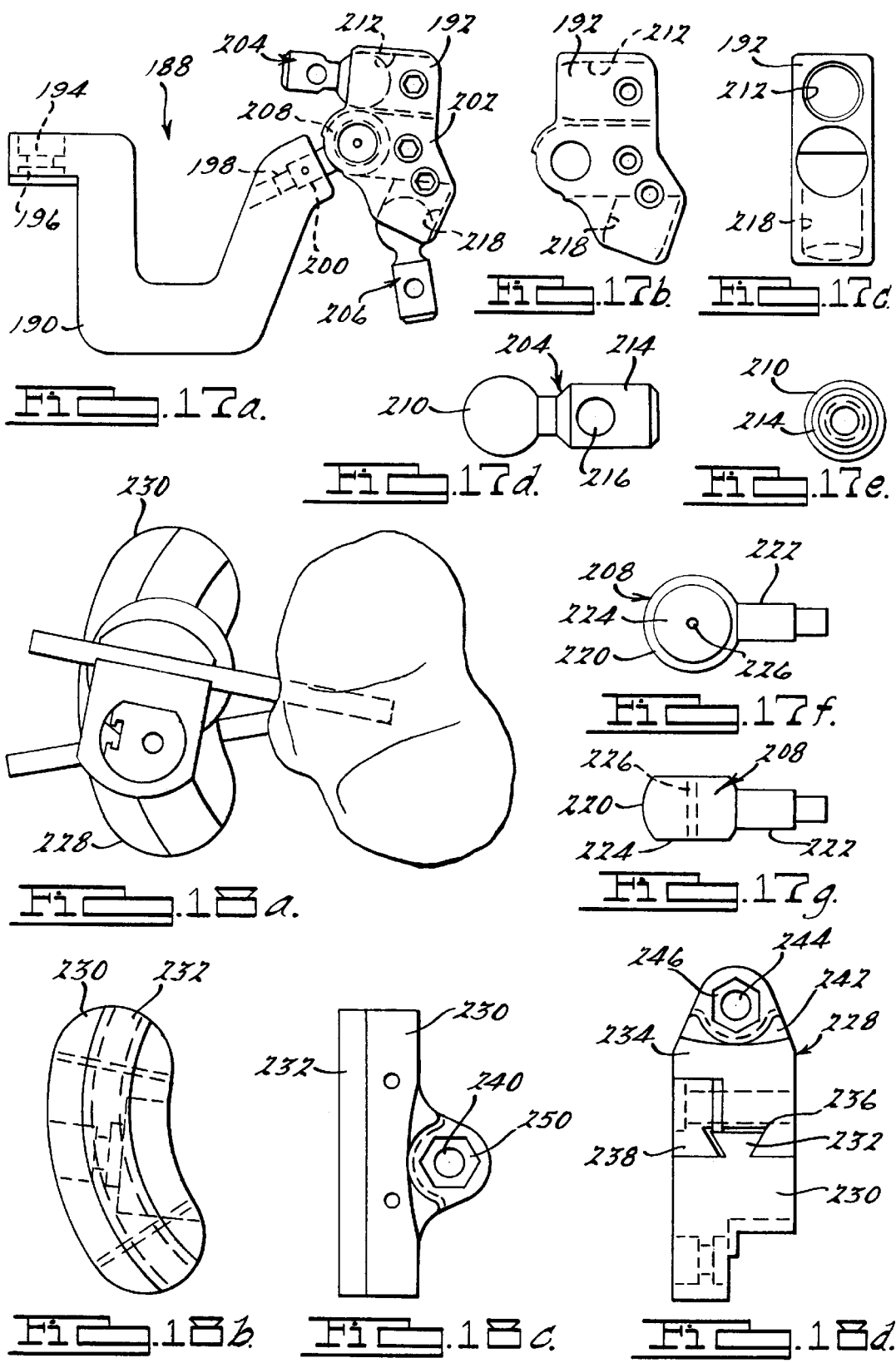

METHOD AND APPARATUS FOR EXTERNAL FIXATION OF LARGE BONES

This is a division of U.S. patent application Ser. No. 08/439,707, filed May 12, 1995 now U.S. Pat. No. 5,662,650.

BACKGROUND OF THE INVENTION

1. Field of the Invention

The present invention relates to an external fixator for use in orthopedic surgical applications, and more particularly to a method and apparatus for external fixation of large bones.

2. Discussion of the Related Art

In various orthopedic surgical procedures, it is often necessary to secure two bone portions in a relatively fixed relationship to each other. The need for establishing such a secured relationship is often a result of a fracture which has occurred to the bone. To ensure that the bone can regenerate in the proper orientation and fuse the fracture, it is important that the bone portions be fixed and in the desired position during bone regeneration.

Various devices are known for the fixation of bone during surgical procedures. For example, the various fixators manufactured by Orthofix S.r.l. for large bones include a bone screw mount which is connected by a ball joint to a central body which is telescopically extendable. The ball joint is able to secure the angularly position of the bone screw mount relative to the central body. The central body of the fixator has two components which are able to be telescopically displaced with respect to each other so as to selectively position the bone pins in the bone. A compression/distraction mechanism, which comprises a threaded screw, is temporarily placed between the central body and one of the bone screw mounts so as to adjust the amount of compression/distraction. When such a fixator is used, a template which resembled the fixator is initially placed in the region of the bone where the fixator is to be attached. A drill is then used to form the holes, and then the template is removed and the bone screws are installed. The bone screws are then attached to the fixator.

While the fixators of the type described above are effective, such fixators are nevertheless susceptible to improvements that may enhance the performance of the fixator. For example, the ball joint connection of the fixator requires a substantial torque to be applied to a cam mechanism so as to secure the ball joint in one particular orientation. In addition, a torque wrench is often necessary to ensure that the relatively large amount of torque required is placed on the ball joint. Accordingly, it would be desirable to reduce the amount of force required to secure the ball joint.

In addition, this type of fixator does not ensure that compression/distraction forces are in a direction parallel to the central axis of the bone. In other words, if the central axis of the fixator is not aligned with the axis of the bone, the force exerted intended to extend or contract the bone is not generally in an axial direction of the bone. Furthermore, the compression/distraction mechanism can bend when the fixator is expanded or compressed, and also can become disengaged from the fixator during operation. In addition, because only the central body expands, the amount to which the fixator is able to extend is somewhat limited (i.e., generally 4 cm of maximum expansion). Because the fixator required a large template be purchased to align the bone screws prior to attaching the fixator to the screws, the cost of using the fixator is also greater than desirable.

Finally, the use of the ball joints between the central body and the bone screw clamps of the fixator described above had several disadvantages. First, the ball joint allowed only 18 degrees of movement in each direction between the central body and the bone screw clamps. This may be considered limiting and it would be desirable to have a broader range of motion. In addition, the ball joint is retained in such a manner that the ball joint could become disassembled if the collar of the fixator and the central body are accidently rotated with respect to each other. Such disassembly would be clearly disadvantageous since this would happen typically when the fixator is being secured to the patient.

SUMMARY OF THE PRESENT INVENTION

In general, the present invention relates to an external fixator for use as an orthopedic device for stabilizing fractured bone. More specifically, the present invention relates to an external fixator which is operable to secure a first bone portion in a particular position with respect to a second bone portion. The external fixator includes a first means for receiving a bone screw which is secure to the first bone portion. The first means for receiving a bone screw is operable to both serve as a template for drilling a hole in the first bone portion for receiving the first bone screw as well as permanently clamp the first bone screw once the first bone screw is attached to the first bone portion. In addition, the external fixator includes a second means for receiving a second bone screw which is secured to the second bone portion. The second means for receiving a second bone screw is operable to both serve as a template for drilling a hole in the second bone portion which is able to receive the second bone screw as well as permanently clamp the second bone screw once the second bone screw is attached to the second bone portion. The external fixator also includes a main body which is operable to connect the first means for receiving the first bone screw with a second means for receiving the second bone screw.

An advantage of the present invention is the provision of a method and apparatus for fixation of bone which does not require a template for drilling holes in the bone for bone screws.

Another advantage of the present invention is the provision of a method and apparatus for fixation of bone in which the bone can be compressed and distracted along the axial length of the bone when the main body of the fixator is not axially aligned with the bone.

Another advantage of the present invention is the provision of a method and apparatus for fixation of bone in which the bone screw clamp may be more securely connected to a main body.

Another advantage of the present invention is the provision of a method and apparatus for external fixation of bone in which the rotational movement of the bone screw clamp with respect to the main body is increased.

Another advantage of the present invention is the provision of a method and apparatus for fixation of bone in which the fixator can be elongated by a relatively large amount.

Another advantage of the present invention is the provision of a method and apparatus for fixation of bone in which the bone screws are more securely held by the fixator.

Additional advantages and features of the present invention will become apparent from the following description and appended claims, taken in conjunction with the accompanying drawings.

BRIEF DESCRIPTION OF THE DRAWINGS

FIG. 1 is an elevational view of the apparatus for external fixation of bone according to the teachings of the preferred embodiment of the present invention shown in operative association with a human tibia;

FIG. 2 is an elevational view of the apparatus for external fixation of bone according to the teachings of the preferred embodiment of the present invention;

FIG. 3 is an end view of the apparatus for external fixation of bone shown in FIG. 2 according to the teachings of the preferred embodiment of the present invention;

FIGS. 4(a) and b are illustrations showing one of the grooved locking washers shown in FIG. 2 according to the teachings of the preferred embodiment of the present invention;

FIGS. 14(a)–(c) are illustrations of the T-shaped module used in conjunction with the apparatus for external fixation of bone according to teachings of preferred embodiment of the present invention;

FIGS. 15(a)–(e) are illustrations of the convergent T-shaped module used in conjunction with the apparatus for external fixation of bone according to teachings of preferred embodiment of the present invention;

FIGS. 16(a)–(e) are illustrations of the self-aligning module used in conjunction with the apparatus for external fixation of bone according to teachings of preferred embodiment of the present invention;

FIGS. 17(a)–(g) are illustrations of the ankle fixator module used in conjunction with the apparatus for external fixation of bone according to teachings of preferred embodiment of the present invention;

FIGS. 18(a)–18(d) are illustrations of the rotational module used in conjunction with the apparatus for external fixation of bone according to teachings of preferred embodiment of the present invention;

DETAILED DESCRIPTION OF THE PREFERRED EMBODIMENT

Figure 5A:
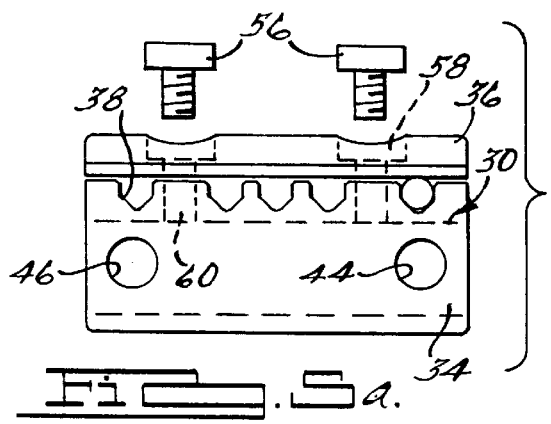
FIGS. 5(a)–(c) are illustrations showing the main body of the bone screw clamp shown in FIG. 2 according to the teaching of the preferred embodiment of the present invention.

The following description of the preferred embodiment of the present invention is merely exemplary in nature and is in no way intended to limit the invention or its application or uses.

Referring to FIG. 1, an apparatus 20 for fixation of a large bone 22 is shown. The apparatus 20 is connected to the bone 22 through a plurality of bone screws 24a and 24b which serve to secure a first bone portion 22a relative to a second bone portion 22b. By securing the first and second bone portions 22a and 22b in this manner, the fracture sites which are located between the first and second bone portions 22a and 22b may be stabilized so as to allow for proper bone regrowth. As evidenced by the drawings, the bone 22 is surrounded by soft tissue 26 and represents a human tibia. It is to be understood, however, that the apparatus 20 may be used with a variety of other types of fractures and a variety of other types of bones as well.

The apparatus 20 comprises a main body 28 as well as a first bone screw clamp 30 and a second bone screw clamp 32. The main body 28 serves to allow the apparatus 20 to axially rotate so as to provide a proper longitudinal rotational location of the bone screws 24 with respect to the bone 22. The first bone screw clamp 30 is used to secure a first bone screw 24a to the apparatus 20 while permitting the first bone screw 24a to be axially displaced from the main body 28. In a similar fashion, the second bone screw clamp 32 which is also able to secure a second bone screw 24b to the apparatus 20 as well as to allow the second bone screw 24b to be axially displaced with respect to the main body 28. The main body 28 as well as the first and second bone screw clamps 30 and 32 will be more fully discussed below.

Figure 5B:
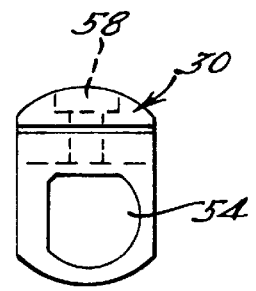
Figure 5C:
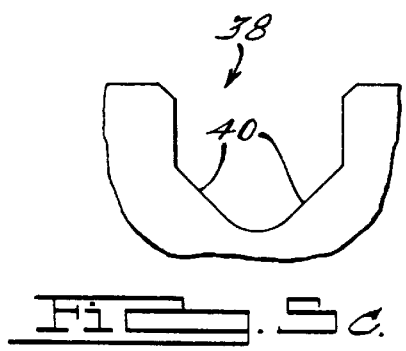
Figure 6:
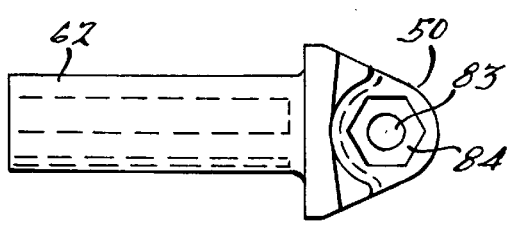
FIG. 6 and FIGS. 7(a)–(c) are illustrations of a first rail member of the bone screw clamp shown in FIG. 2 according to the teaching of the preferred embodiment of the present invention.
Figure 7A:
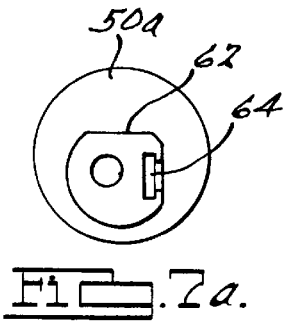
Figure 7B:
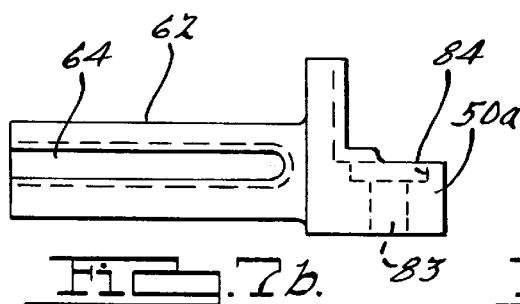
Figure 7C:
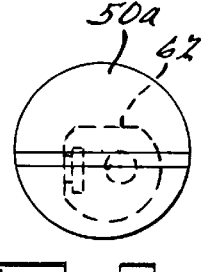
Figure 8:
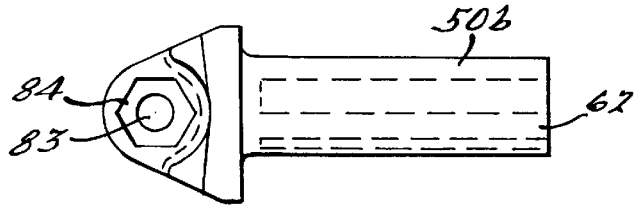
FIG. 8 and FIGS. 9(a)–(c) are illustrations of the second rail member used in conjunction with the bone screw clamp shown in FIG. 2 according to the teachings of the preferred embodiment of the present invention.
Figure 21:
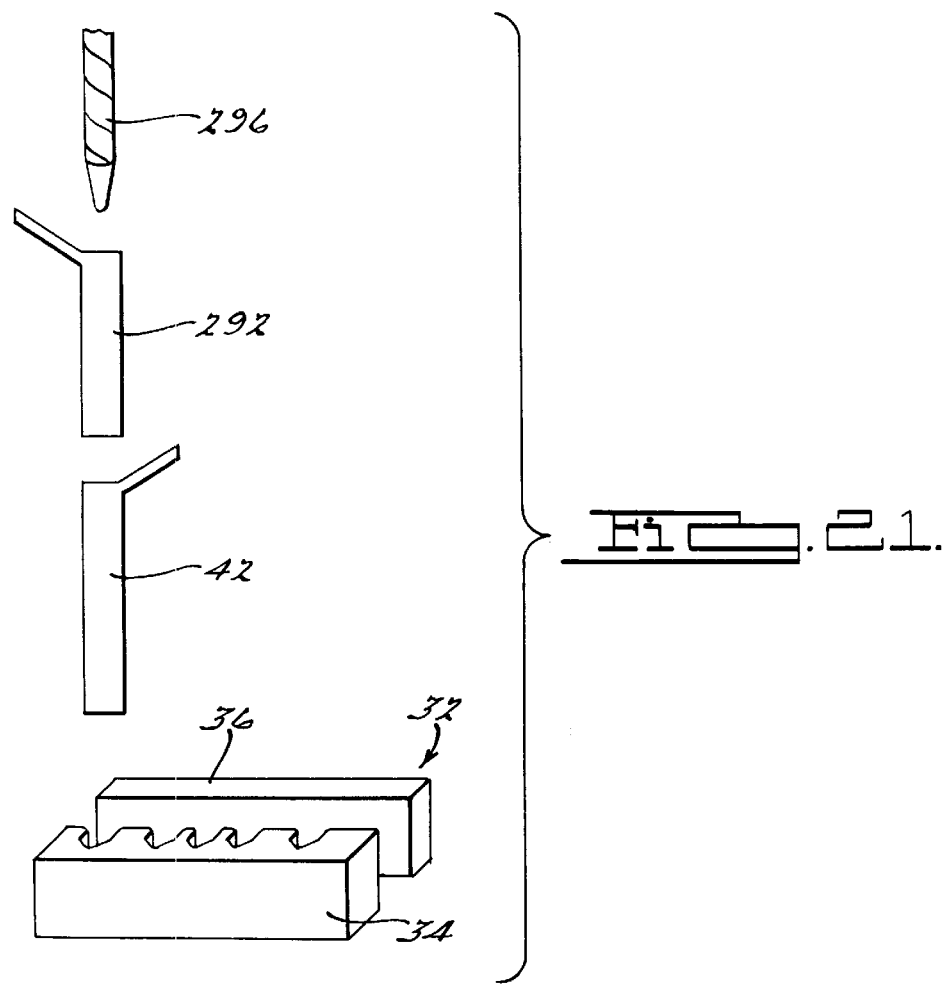
FIG. 21 is an exploded view showing the operation of the bone clamp to serve as a template for drilling a hole in the bone according to the teachings of the preferred embodiment of the present invention.

The first bone screw clamp 30 will be described in greater detail with reference to FIGS. 5(a)–5(c). It is to be understood that while only the first bone screw clamp 30 is being described, the second bone screw clamp 32 will have a similar construction. The first bone screw clamp 30 includes a base portion 34 and a cover portion 36. The base portion 34 serves to receive the first bone screw 24a in one of a plurality of grooves 38, while the cover portion 36 serves to secure the first bone screw 24a within the grooves 38. As shown in FIG. 5(c), the grooves 38 include two contact surfaces 40 which are substantially planar so as to permit line contact of the first bone screw 24a in two positions within the grooves 38. Since the first bone screw 24a also engages the cover portion 36 of the bone screw clamp 30, the first bone screw 24a engages the first bone screw clamp 30 in three positions (i.e., along the contact surfaces 40 as well as on the cover portion 36). This provides line contact for the bone screw 24 which secures the bone screws 24 in a more effective manner than if the grooves 38 were cylindrical. This is because if the grooves 38 were cylindrical, they would only contact the bone screw 24 in two positions (i.e., one contact surface in the groove 38 and one contact surface on the cover portion 36) since it was generally not possible to have the shape of the groove 38 exactly match the shape of the bone screw 24. In addition, the grooves 38 are able to accommodate a soft tissue sleeve 42 (shown in FIG. 21) so that the bone screw clamp 30 may also serve as a template as will be more fully discussed below.

The base portion 34 of the bone screw clamp 30 further includes a first aperture 44 and a second aperture 46. The first aperture 44 is used to receive a threaded member 48 which serves to secure a rail member 50 in a locked position as will be more fully discussed below. The second aperture 46 is also used to receive a threaded member which is able to secure a compression/distraction member 52 (shown in FIGS. 10(a)–(b) within a D-shaped central bore 54 of the bone screw clamp 30. The compression/distraction member 52 will also be described more fully below.

The cover portion 36 of the first bone screw clamp 30 is secured to the base portion 34 of the first bone screw clamp 30 by means of two screws 56. To accommodate these screws 56, the cover portion 36 of the bone screw clamp 30 includes two apertures 58 (shown in phantom in FIG. 5(a)) which mate with corresponding apertures 60 in the base portion 34 of the bone screw clamp 30. Accordingly, upon secured threaded engagement of the screws 56 within the apertures 58 and 60, the cover portion 36 of the bone screw clamp 30 may be secured to the base portion 34 of the bone screw clamp 30.

To provide means for laterally displacing the first bone screw clamp 30 with respect to the main body 28, the bone screw clamp 30 further includes a first rail member 50. The first rail member 50a includes a D-shaped extension 62 which is able to receive in the D-shaped bore 54 of the bone screw clamp 30. Because of the cross-sectional shape of the D-shaped extension 62, the base portion 34 of the bone screw clamp 30 is able to slide on the D-shaped extension 62 of the rail member 50a, though the base portion 34 is unable to rotate with respect to the D-shaped extension 62.

The first rail member 50a further includes a groove 64 which is disposed on the surface of the D-shaped extension 62. The location of the groove 64 is such as to permit the groove 64 to be located adjacent to the aperture 44 when the D-shaped extension 62 of the first rail member 50a is inserted into the D-shaped bore 54 of the base portion 34. As will be apparent to those skilled in the art, the threaded member 48 can then be inserted into the aperture 44 of the base portion 34 of the bone screw clamp 30 so as to securely engage the groove 64 of the D-shaped extension 62 thereby preventing axial movement of the base portion 34 with respect to the first rail member 50a.

To provide means for displacing the second bone screw clamp 32 with respect to the main body 28, the second bone screw clamp 32 also includes a second rail member 50b. As with the first rail member 50a, the second rail member 50b has a D-shaped extension 62 which is able to receive the D-shaped bore 54 of the second bone screw clamp 32. Because of the cross-sectional shape of the D-shaped extension 62, the base portion 34 of the second bone screw clamp 32 is able to slide on the D-shaped extension 62 of the second rail member 50b, though the base portion 34 is unable to rotate with respect to the D-shaped extension 62.

The second rail member 50b further includes a groove 64 which is disposed on the surface of the D-shaped extension 62. In a manner similar to the first rail member 50a, the location of the groove 64 is such as to permit the groove 64 to be located adjacent to the aperture 44 when the D-shaped extension 62 of the second rail member 50b is inserted into the D-shaped bore 54 of the base portion 34. The threaded member 48 can then be inserted into the aperture 44 of the base portion 34 so as to securely engage the groove 64 of the D-shaped extension 62 thereby preventing axial movement of the base portion 34 with respect to the second rail member 50b.

Figure 10A:
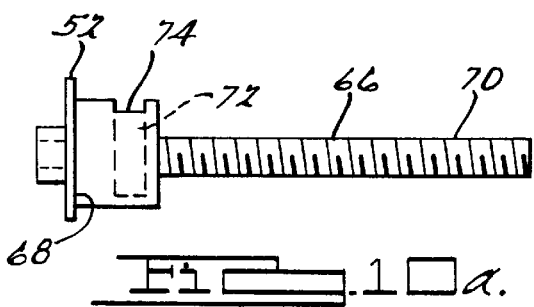
FIGS. 10(a)–(b) are illustrations of the compression/distraction mechanism of the bone screw clamp shown in FIG. 2 according to the teachings of the preferred embodiment of the present invention.
Figure 10B:
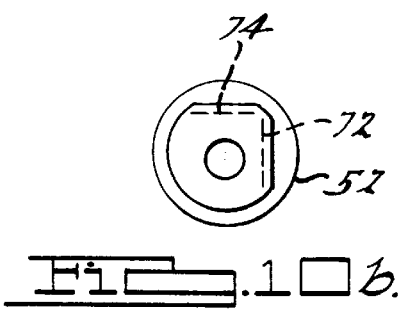
Figure 11A:
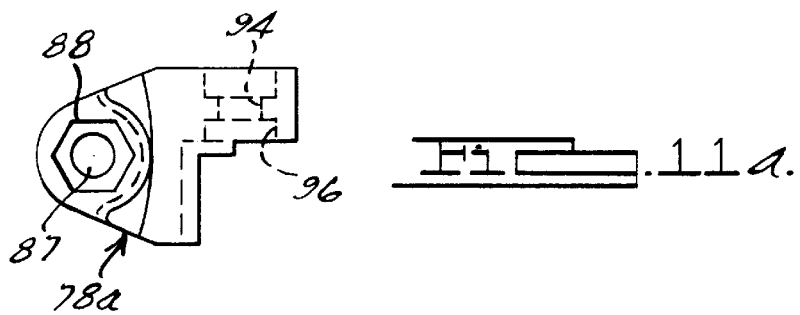
FIGS. 11(a)–(c) are illustrations of the first and second clamp connection members shown in FIG. 2 according to the teachings of the preferred embodiment of the present invention.
Figure 11B:
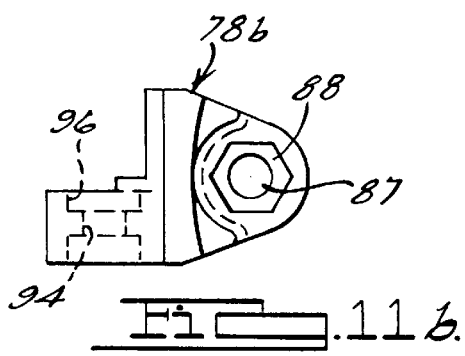
Figure 11C:
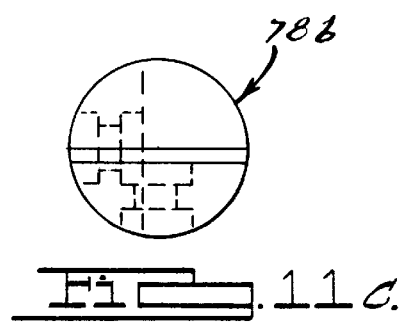
Figure 12A:
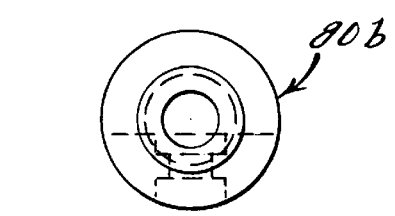
FIGS. 12(a)–(c) are illustrations of the first rotational component of the main body shown in FIG. 2 used in conjunction with the apparatus for external fixation of bone according to the teachings of the preferred embodiment of the present invention.
Figure 12B:
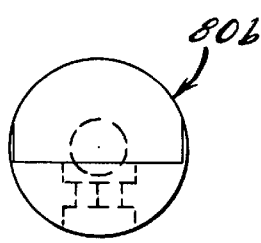
Figure 12C:
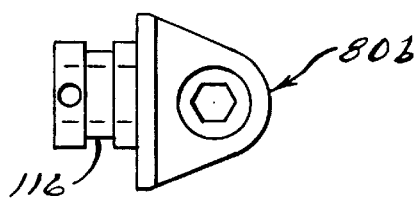
Figure 13:
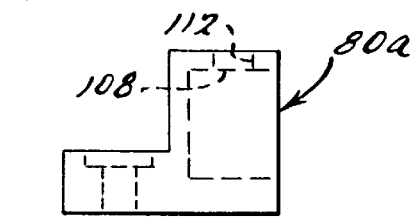
FIG. 13 is an illustration of the second rotational component of the main body shown in FIG. 2 used in conjunction with the apparatus for external fixation of bone according to the teachings of the preferred embodiment of the present invention.

To provide means for controlling the displacement of the base member 34 of the first and second bone screw clamps 30 and 32 with respect to the first and second rail members 50a and 50b, respectively, the first and second bone screw clamps 30 and 32 are each able to operatively engage a compression/distraction mechanisms 52 shown in FIGS. 10(a)–10(b). The compression/distraction mechanism 52 includes a threaded member 66 having a head portion 68 and a threaded portion 70. In addition, the compression/ distraction mechanism 52 includes a central body 72 having two flats 74 (shown in phantom in FIG. 10b) which are rotationally independent from the threaded portion 70. The threaded portion 70 is able to threadably engage a central bore 76 of the first rail member 50a. In addition, the central body 72 of the compression/distraction mechanism 52 is able to be secured in the D-shaped bore 54 of the base portion 34 of the first bone screw clamp 30 by means of a threaded fastener 48 inserted through the aperture 44 of the base portion 34 of the first bone screw clamp 30. Upon rotation of the threaded portion 70 of the compression/ distraction mechanism 52, it will be apparent that the base portion 34 of the first bone screw clamp 30 will be displaced with respect to the first rail member 50a.

The main body 28 will now be described in greater detail. The main body 28 includes a first and second bone screw clamp connection members 78a and 78b, respectively, as well as a first and second rotational components 80a and 80b. The first and second bone screw clamp connection members 78a and 78b serve to secure the main body 28 to the first and second rail members 50a and 50b, respectively. In this regard, a plurality of grooved locking washers 82 are disposed between the first rail member 50a and the first bone clamp connection member 78a, as well as between the second rail member 50b and the second bone clamp connection member 78b. In particular, the first rail member 50a has an aperture 83 with a hex-shaped recess 84 for receiving the base portion 86 of the washer 82, while the second rail member 50b also has an aperture 83 with a hex-shaped recess 84 for receiving the base portion 86 of the washer 82. In a similar fashion, the first bone screw clamp connection member 78a also includes an aperture 87 with a hex-shaped recess 88 for receiving the base portion 86 of the washer 82, while the second bone screw clamp connection member 78b also has an aperture 87 with a hex-shaped recess 88 for engaging the base portion 86 of the washer 82. Because the groove surface 90 of the washer 82 engage each other, the first rail member 50a is secured to the first bone clamp connection member 78a upon secured threaded engagement of a screw 92, while the second rail member 50(b) is secured to the second bone clamp connection member 78b upon threaded engagement of the screw 92. The first and second bone screw clamp connection members 78a and 78b permit approximately 60° of relative rotation between the first and second bone screw clamps 30 and 32 with respect to the central body 28.

The first and second bone screw clamp connection members 78a and 78b are also secured to the first rotational component and second rotational component 80a and 80b, respectively, by a plurality of locking washers 82. In this regard, first bone screw clamp connection member 78a includes an aperture with a hex-shaped recess 96 for receiving the base portion 86 of the washer 82, while the second bone screw clamp connection member 78b similarly has an aperture 94 with a hex-shaped recess 96 for receiving the base portion 86 of the washer 82. In a similar fashion, the first rotational component 80a also has an aperture 98 with a hex-shaped recess 100 for receiving the base portion 86 of the washer 82, while the second rotational component also has an aperture 102 with a hex-shaped recess 104 for receiving the base portion 86 of the washer 82. The grooves 90 in the washers 82 allow more secure attachment between the first and second bone screw clamp connection members 78a and 78b and the first and second rotational components 80a and 80b, respectively, when they are secured by the bolts 106.

The first rotational component 80b includes a bore 108 which is able to receive a portion 110 of the second rotational component 80a and includes an aperture 112 which is able to receive a threaded member 114 (shown in FIG. 1). The second rotational component 80b includes a groove 116 which is able to be located proximate to the aperture 112 in the first rotational component 80a. Accordingly, when the threaded member 114 is inserted through the aperture 112 in the first rotational component 80a and is allowed to engage the groove 116 in the second rotational component 80b, the first and second rotational components 80a and 80b are securely locked so as to prohibit further rotational movement of the first rotational component 80a with respect to the second rotational component 80b. Accordingly, longitudinal rotation of the first and second bone screw clamps 30 and 32 may be achieved by loosening the threaded member 114 in the aperture 112 of the first rotational component 80a, thereby allowing the first and second rotational components 80a and 80b to rotate.

Various modules may be used in conjunction with the apparatus 20 to accommodate different fractures. For example, the apparatus 20 may also include a T-shaped module 118 of the type shown in FIGS. 14(a)–14(c). The T-shaped module 118 includes a base portion 120 as well as a cover portion 122. The base portion 120 includes a plurality of grooves 124 of the type which are similar to the grooves 38 described in conjunction with the first and second bone screw clamps 30 and 32. In addition, the cover portion 122 is operable to secure bone screws (not shown) which are located in the grooves 124 to the base portion 120. The cover portion 122 and the base portion 120 are secured by means of a threaded fastener 48 which is not shown. The T-shaped module 118 includes an extension member 126 which includes a threaded aperture 128 with a hex-shaped recess 130 which permits the T-shaped module 118 to be secured to the first bone screw clamp 30 connection member of the main body 28. In this regard, the hex-shaped recess 130 is used to receive the base portion 86 of the locking washer 82 which has a grooved surface 90 which engages the groove surface 90 of a locking washer 82 disposed on the first bone screw clamp connection member 78a. Accordingly, a threaded fastener (not shown) which passes through the aperture 128 in the extension member 126 as well as the aperture 87 in the first bone screw clamp connection member 78a secures the T-shaped module 118 to the first bone screw clamp connection member 78a. The cover portion 122 includes a pair of apertures 132 which align with a pair of apertures 134 in the base portion 120 for receiving threaded fasteners (not shown) and securing the cover portion 122 to the base portion 120.

The apparatus 20 may also comprise a convergent T-shaped module 136 which is shown in FIGS. 15(a)–15(e). The convergent T-shaped module 136 allows the bone screws 24 which are held by the convergent T-shaped module 136 to be angularly displaced with respect to each other. The convergent T-shaped module 136 includes a first arm member 138 which is able to be rotationally displaced with respect to a second arm member 140. The first arm member 138 includes a first plurality of grooves 142 which are able to accommodate a plurality of bone screws in a manner discussed above. Bone screws which are disposed within the first arm member 138 are secured within the grooves 142 by means of a first cover portion 144. A threaded fastener 48 may be passed through an aperture 146 in the first cover portion 144 and an aperture 148 in the first arm member for securing the first cover portion 144 to the first arm member 138 and therefore the bone screws within the grooves 142. The second arm 140 of the convergent T-shaped module member 136 has a second plurality of grooves 150. The second plurality of grooves 150 are disposed on the second arm member 136 at a position which is axially offset from the position of the first plurality of grooves 142 in the first arm member 138. The offset in the position of the second plurality of grooves 150 with respect to the first plurality of grooves 142 serves to allow bone screws 24 located in the first and second plurality of grooves 142 and 150 to move in a direction towards each other without contacting each other. The bone screws which are located in the second arm member 140 are secured within the second plurality of grooves 150 by means of a second cover portion 152. The second cover portion 152 includes a plurality of downwardly extending projections 154 which engage the bone screws within the second plurality of grooves 150 while accommodating the difference in depth of the grooves 150. The second cover portion 152 includes an aperture 155 which aligns with a corresponding aperture 157 for receiving a fastener (not shown). The first arm member 138 and the second arm member 140 are secured to each other by means of two locking washers 82 and a threaded fastener (not shown) which is secured through an aperture 156 in the first arm member 138 and an aperture 158 in the second arm member 140. In this regard, the aperture 158 in the second arm member 140 includes a recess 160 for receiving the base portion 86 of a locking washer 82, while the aperture 156 in the first arm member 138 also includes a recess 162 for receiving the base portion 86 of a locking washer 82. Finally, the first arm member 138 further includes a second aperture 164 having a hex-shaped recess 166 which is able to receive a fastener (not shown) and a locking washer 82 so as to secure the convergent T-shaped module 136 to the first bone screw clamp connection member 78a in the manner described above.

The apparatus 20 may further include a self-adjusting module 168 of the type which is shown in FIGS. 16(a)–16(e). The self-adjusting module 168 is used to allow for rotational movement of another component (such as the T-shaped module 118) with respect to the main body 28 of the apparatus 20. The self-adjusting module 168 includes a male component 170 and a female component 172. The male component 170 of the self-adjusting module 168 includes an aperture 174 having a hex-shaped recess 176 which is able to be secured to the first bone screw clamp connection member 78a by means of a threaded fastener (not shown) 48 and a locking washer 82. The male component 170 also includes an extension member 178 which is able to be received between two projections 180 which are disposed on the female component 172 of the self-adjusting component 168. The male and female components 170 and 172 are connected to each other by means of a threaded fastener (not shown) which is disposed between the first and second projections 180 and which passes through an elongated slot in the male component 182. Because of the presence of the slot, the female component 172 may rotate and move laterally with respect to the male component 170. The female component 172 may be connected to another module by means of a threaded fastener 48 (not shown) which is disposed in an aperture 184 having a hex-shaped recess 186 for receiving the base portion 86 of a locking washer 82.

The apparatus 20 may also include an ankle fixator module 188 similar to that shown in FIGS. 17(a)–17(g). In this regard, the ankle fixator module 188 includes a fixator support member 190 as well as an ankle support member 192. The fixator support member 190 is secured to the first rail support member 50a by means of a threaded fastener 48 located in an aperture 194 having a hex-shaped recess 196 for receiving the base portion 86 of a locking washer 82. The fixator support member 190 is generally U-shaped so as to allow greater radiographic examination of the ankle. The fixator support member 190 further includes an aperture 198 which is able to receive a portion 200 of the ankle support member 192 as discussed below.

The ankle support member of the ankle fixator module 188 includes a body portion 202 as well as two bone screw clamp members 204 and 206 and a part spherical connector 208. The first bone screw clamp member 204 includes a spherical portion 210 which is able to be inserted into an aperture 212 located in the body portion 202 so as to allow the spherical portion 210 to rotate. The bone screw clamp member 204 includes an extension portion 214 having an aperture 216 through which a bone screw may be inserted. The bone screw is secured within the aperture 216 of the extension portion 214 by means of a locking screw (not shown) which extends inward from the end of the extension portion 214 into the aperture 216. A bushing (not shown) may also be located within the aperture 216 of the extension portion 214 so as to change the diameter of the aperture 216 between the screw guide and a bone screw in a manner similar to that discussed below. The first bone screw clamp member 204 is able to be positionally secured to the body portion 202 by means of a cam mechanism well known to those skilled in the art. The second bone screw clamp member 206 is disposed within a second aperture 218 of the body portion 202. The second bone screw clamp member 206 is similar to the first bone screw clamp member 204 in that it is able to receive and secure a bone screw. The second bone clamp member 206 is also secured to the body portion 202 by means of the cam mechanism.

The part spherical connector 208 of the ankle support member 192 is used to secure the fixator support member 190 to the body portion 202. The part spherical connector 208 includes a part spherical portion 220 as well as an extension portion 222. The part spherical portion includes two flats 224 which allow rotation of the body portion 202 with respect to the fixator support member 190 in a single plane. The part spherical portion 208 includes an aperture 226 which is able to receive a K-wire (not shown) during implantation. In this regard, when the ankle fixator module 188 is used, a K-wire is first inserted through the aperture 226 in the part spherical portion 208 and into the rotational axis of the ankle. A bone screw is then inserted and secured to each of the bone clamp members 204 and 206 and then the bone screws 24 are secured by means of the cam mechanism. The part spherical connector 208 is then secured also by a cam mechanism. Once the bone screw clamps 204 and 206 and the part spherical connector 208 are positionally secured, the K-wire is removed from the aperture 226.

The apparatus 20 may also include a rotational module 228 shown in FIGS. 18(a)–18(c) which is able to allow a bone screw to be placed at a position which is defined around the axis of the bone. The rotational module 228 includes a track member 230 having a dovetail-shaped track 232. The dovetail-shaped track 232 is located in such a fashion so as to extend from an approximately constant radius from the longitudinal axis of the bone. The rotational module 228 further includes a sliding member 234 which includes a groove 236 which is able to be received in the track 232 of the track member 230. The sliding member 234 includes a securing member 238 which allows the sliding member 234 to be removably attached to the track 232. The sliding member 234 is attached to the track member 230 by means of a threaded fastener which is able to be inserted through an aperture 240 in the track member 230 as well as the attachment portion of the bone screw support member. In addition, another module may be attached to the sliding member 234 by means of an attachment portion 242 which extends from the sliding member 234. The attachment portion 242 includes an aperture 244 which is able to receive a threaded fastener 48 and includes a hex-shaped recess 246 for receiving the base 86 of a washer 82.

In use, the attachment portion 242 of the track member 230 is secured to the first bone screw clamp connection member 70a by means of a threaded fastener 48 which is inserted through the aperture 240 in the track member 230 having a hex-shaped recess 250 for receiving the base portion 86 of a locking washer 82. The sliding member 234 is able to be displaced on the track 232 to the desired position. The sliding member 234 is then secured in the proper position with respect to the track member 230 and then another module or a bone screw clamp may be secured to the attachment portion 242 of the sliding member 234.

Figure 19A:
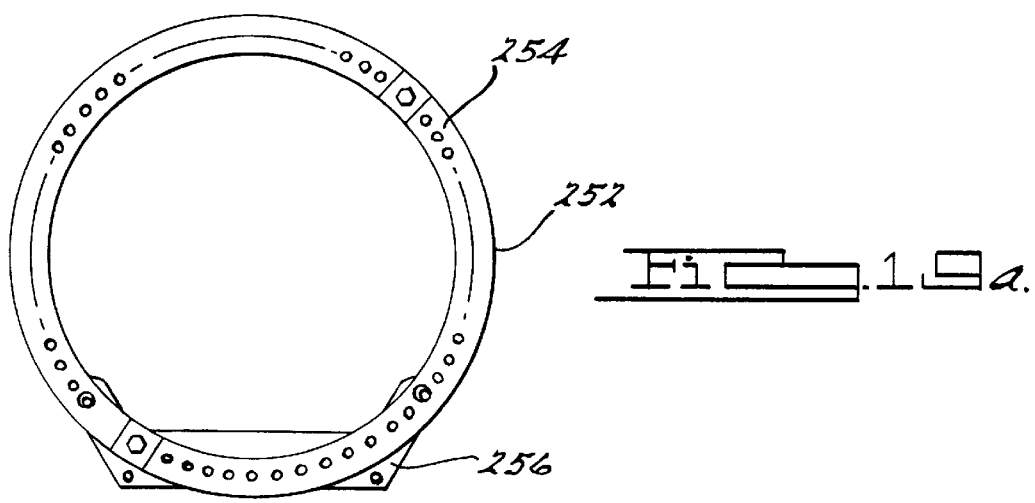
FIGS. 19(a)–(e) are illustrations of the ring-adaptor module used in conjunction with the apparatus for external fixation of bone according to teachings of preferred embodiment of the present invention.
Figure 19B:
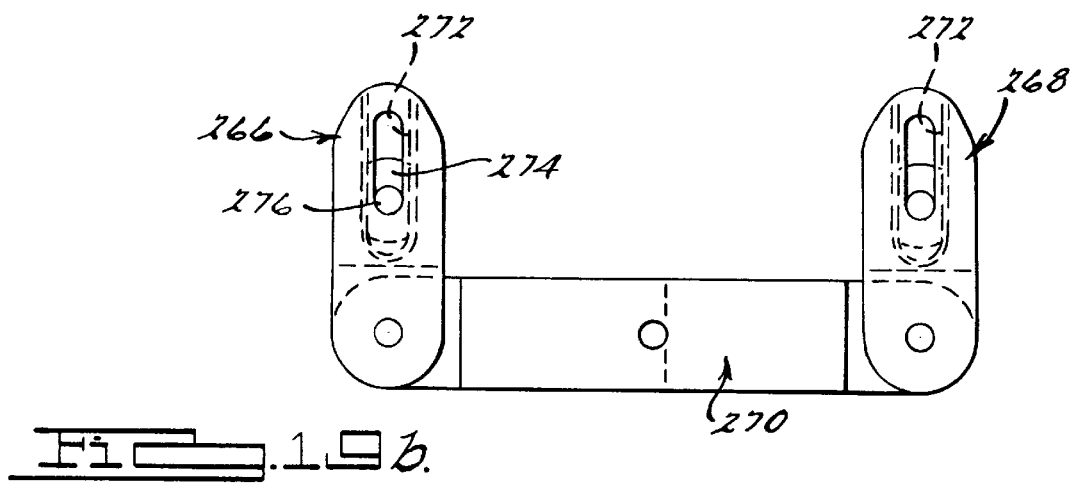
Figure 19C:
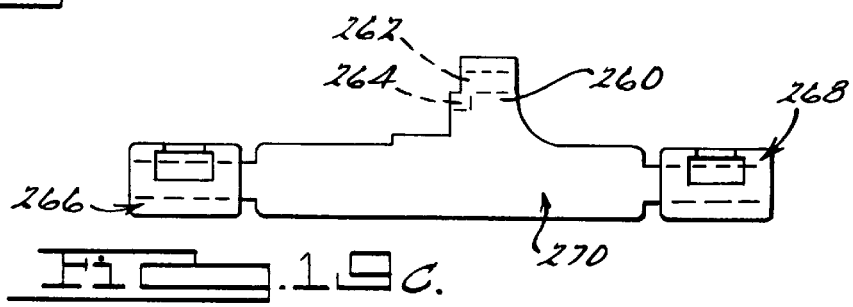
Figure 19D:
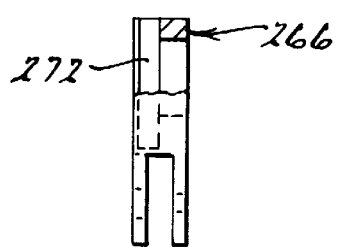
Figure 19E:
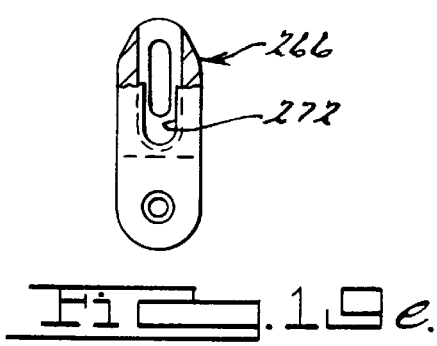

The apparatus 20 may also include a ring adaptor module 252 of the type shown in FIGS. 19(a)–19(c). The ring adaptor module 252 includes a ring 254 which is used to surround a limb so that bone screws inserted into a bone may be secured to the ring 254. The ring adaptor module 252 also includes a connection assembly 256. The connection assembly 256 includes an attachment portion 260 which is operable to be secured to the first bone screw clamp connection member 78a by a threaded fastener which is able to be received in an aperture 262 in the connection assembly 256 and has a hex-shaped recess 264 for receiving the base 86 of a locking washer 82. The connection assembly 256 further includes two arm members 266 and 268 which extend from a body member 270. The arm members 266 and 268 are able to rotate with respect to the body member 270 and include a recess 272 for receiving an oblong head 274 of a ring-mount screw 276. The head 274 of the ring-mount screw 276 is able to slide within the recess 272 of the arm members 266 and 268 but is able to be attached to the ring 254 by means of a threaded end portion 278 on the ring mount screw 276.

Figure 20:
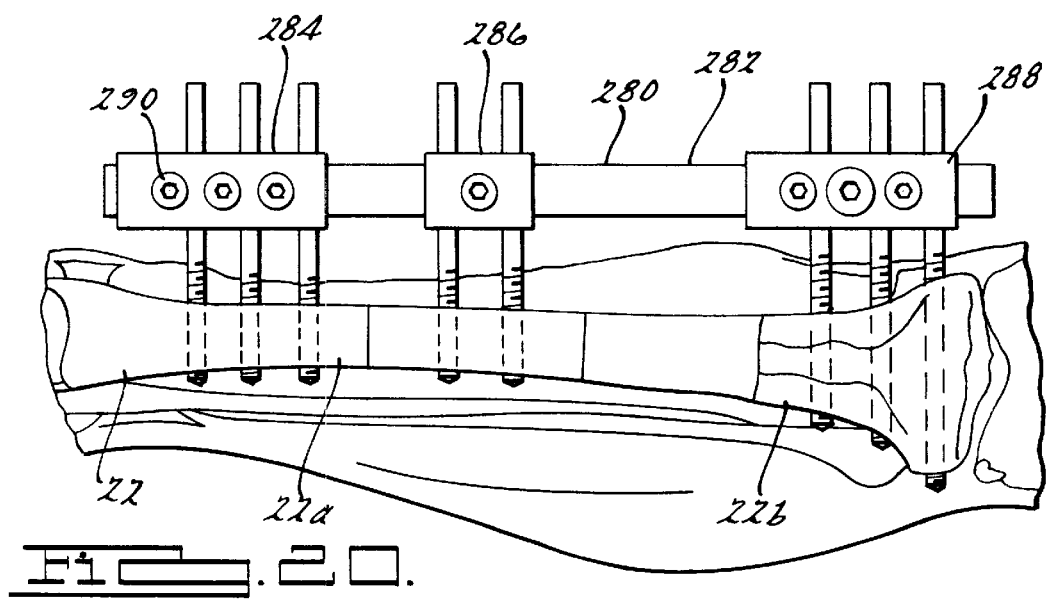
FIG. 20 is an illustration of the bone transport module used in conjunction with the apparatus for external fixation of bone according to teachings of preferred embodiment of the present invention.

The apparatus 20 may also be used in conjunction with a bone transport device 280 similar to that shown in FIG. 20. The bone transport device 280 includes a longitudinal member 282 as well as a first bone screw clamp 284, a second bone screw clamp 286 and a third bone screw clamp 288. The bone screw clamps 284, 286, 288 are able to be longitudinally displaced on the longitudinal member 282 so as to be positioned adjacent to the desired portion of bone 22. The bone screw clamps 284, 286, 288 may be secured to the longitudinal member 282 by means of a threaded fastener and locking washer 82 similar to that described above. In use, the first and third bone screw clamps 284, 288 are placed in a location proximate to the first bone portion 22a and a second bone portion 22b. The second bone screw clamp 286 is then incrementally moved from the position proximate the first bone screw clamp 284 to a position proximate the third bone screw clamp 288 in a manner to stimulate bone growth as is well known by those skilled in the art.

Figure 9A:
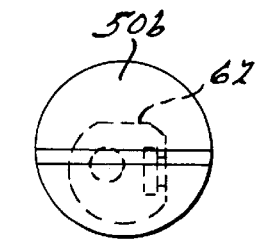
Figure 9B:
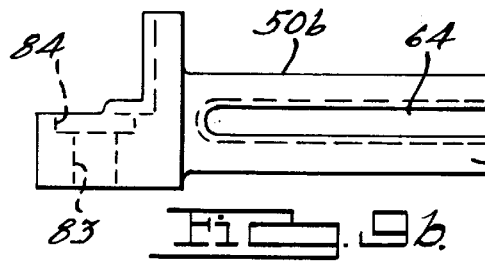
Figure 9C:
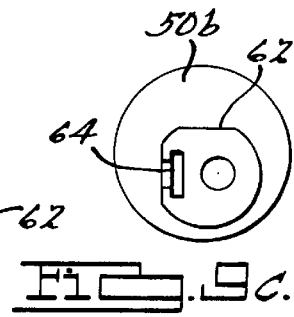

In use, the apparatus 20 is able to be secured to the bone 22 without using a separate template. This is accomplished by allowing the various elements which are to receive bone screws 24 to also accommodate for a soft tissue guide 42 as well as a drill guide 292. This is illustrated in FIG. 9 with respect to the bone screw clamp 32, though it is to be understood that other components, such as to the components associated with the ankle fixation module 188, may also use a similar mechanism. When it is desired to position the bone screw, the soft tissue guide 42 is inserted between the base portion 34 and the cover portion 36 of the bone screw clamp 32. A drill guide 292 is then inserted through the soft tissue guide 42 and then a drill 296 is used to drill the hole in the bone 22 of appropriate depth. The drill 296 is then removed as is the drill guide 292 and then the bone screw is inserted into the soft tissue guide 42. Once the bone screw has been secured to the bone, the soft tissue guide 42 is removed from the bone screw clamp 32 and then the bone screw clamp 32 is more tightly secured to the bone screw. By using this procedure, a separate template is not needed for proper orientation of the bone screws 24.

The foregoing discussion discloses and describes merely exemplary embodiments of the present invention. One skilled in the art will recognize from such discussion and from the accompanying drawings and claims, that various changes, modifications and variations can be made therein without departing from the spirit and scope of the invention.

What is claimed is:

1. An apparatus for external fixation of an ankle joint having an anatomical pivot axis interdisposed between first and second skeletal elements by a first bone screw connected to the first skeletal element and a second bone screw connected to the second skeletal element, the apparatus comprising:

a first clamping member for receiving the first bone screw;

a second clamping member for receiving the second bone screw; and a connecting member for securing said first clamping member to said second clamping member, said connecting member having a substantially U-shaped configuration for at least partially defining a radiographic window to permit radiographic examination of the fixed relationship of the ankle joint in a lateral direction, the anatomical pivot axis being located within said radiographic window.

2. The apparatus for external fixation of an ankle joint of claim 1, wherein said connecting member is pivotally interconnected to said first clamping member for rotation about a first axis.

3. The apparatus for external fixation of an ankle joint of claim 2, wherein said connecting member is pivotally interconnected to said second clamping member for rotation about a second axis.

4. The apparatus for external fixation of an ankle joint of claim 3, wherein said first axis is substantially perpendicular to said second axis.

5. The apparatus for external fixation of an ankle joint of claim 1, wherein said connecting member includes first and second legs interconnected by an intermediate portion, said first and second legs attached to said first and second clamping members, respectively.

6. The apparatus for external fixation of an ankle joint of claim 5, wherein said first and second legs diverge as they extend from said intermediate portion.

7. An apparatus for external fixation of an ankle joint having an anatomical pivot axis interdisposed between first and second skeletal elements by a first bone screw connected to the first skeletal element and a second bone screw connected to the second skeletal element, the apparatus comprising:

a first clamping member for receiving the first bone screw;

a second clamping member for receiving the second bone screw; and a connecting member for securing said first clamping member to said second clamping member, said connecting member having a substantially U-shaped configuration for at least partially defining a radiographic window to permit radiographic examination of the fixed relationship of the ankle joint in a lateral direction, said connecting member including first and second legs interconnected by an intermediate portion, said first and second legs attached to said first and second clamping members, respectively.

8. The apparatus for external fixation of an ankle joint of claim 7, wherein said connecting member is pivotally interconnected to said first clamping member for rotation about a first axis.

9. The apparatus for external fixation of an ankle joint of claim 8, wherein said connecting member is pivotally interconnected to said second clamping member for rotation about a second axis.

10. The apparatus for external fixation of an ankle joint of claim 9, wherein said first axis is substantially perpendicular to said second axis.

11. The apparatus for external fixation of an ankle joint of claim 7, wherein said first and second legs diverge as they extend from said intermediate portion.

12. A method for external fixation of an ankle joint having an anatomical pivot axis interdisposed between first and second skeletal elements, the method comprising the steps of:

providing a first bone screw;

providing a second bone screw;

connecting the first bone screw to the first skeletal element;

connecting the second bone screw to the second skeletal element;

engaging said first bone screw with a first clamping member;

engaging said second bone screw with a second clamping member; and connecting said first and second clamping members with a connection member having a substantially U-shaped configuration defining a radiographic window to permit radiographic examination of the fixed relationship of the ankle joint in a lateral direction, the anatomical pivot axis being located within said radiographic window.

13. The method for external fixation of an ankle of claim 12, wherein the step of connecting the first and second clamping members with a connection member includes the step of pivotally connecting said connection member and said first clamping member for relative rotation about a first pivot axis.

14. The method for external fixation of an ankle of claim 13, wherein the step of connecting the first and second clamping members with a connection member further includes the step of pivotally connecting said connection member and said second clamping member for relative rotation about second pivot axis.

15. The method for external fixation of an ankle of claim 14, wherein said first axis is substantially perpendicular to said second axis.

16. The method for external fixation of an ankle of claim 12, wherein said connection member includes first and second legs interconnected by an intermediate portion, said first and second legs attached to said first and second clamping members, respectively.

* * * * *